United States Patent
Jee et al.

(10) Patent No.: US 10,351,900 B2
(45) Date of Patent: Jul. 16, 2019

(54) METHOD FOR IDENTIFYING PATHOGENS OF BACTERIAL INFECTIOUS DISEASES BY USING BACTERIA-DERIVED NANOVESICLES

(71) Applicant: MD HEALTHCARE INC., Seoul (KR)

(72) Inventors: Young Koo Jee, Seongnam-si (KR); Yoon-Keun Kim, Paju-si (KR); Young-Ju Kim, Seoul (KR); Hyeonil Choi, Pohang-si (KR); Mina Rho, Seoul (KR); Sungmin Kiem, Busan (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 15/535,632

(22) PCT Filed: Dec. 10, 2015

(86) PCT No.: PCT/KR2015/013524
§ 371 (c)(1),
(2) Date: Jun. 13, 2017

(87) PCT Pub. No.: WO2016/099076
PCT Pub. Date: Jun. 23, 2016

(65) Prior Publication Data
US 2017/0369930 A1   Dec. 28, 2017

(30) Foreign Application Priority Data
Dec. 16, 2014   (KR) .................. 10-2014-0181580

(51) Int. Cl.
*C12Q 1/6806*   (2018.01)
*C12N 15/10*   (2006.01)
(Continued)

(52) U.S. Cl.
CPC ....... *C12Q 1/6806* (2013.01); *C12N 15/1003* (2013.01); *C12N 15/88* (2013.01); *C12Q 1/689* (2013.01)

(58) Field of Classification Search
CPC .............. G01N 33/5438; C12Q 1/6825; C12Q 2600/156; C12Q 1/6806; C12Q 1/689;
(Continued)

(56) References Cited

U.S. PATENT DOCUMENTS 6,391,558 B1 * 5/2002 Henkens .............. C12Q 1/6825
435/6.11

FOREIGN PATENT DOCUMENTS

JP       2008-148629 A    7/2008
KR    10-2005-0038856 A    4/2005
(Continued)

OTHER PUBLICATIONS

Moldovan et al., (Methods Mol. Biol. 2013; 1024: 129-145). (Year: 2013).*
(Continued)

*Primary Examiner* — Jana A Hines
(74) *Attorney, Agent, or Firm* — Lucas & Mercanti, LLP (57) ABSTRACT

The present invention relates to a method for predicting causative factors (bacteria) of serious bacterial infectious diseases in a clinical sample containing bacteria-derived nano-sized extracellular vesicles, that is, nanovesicles, through the analysis of the genes contained in the nanovesicles. According to the present invention, information on bacteria of serious bacterial infection can be provided, a causative factor of the bacterial infection can be predicted, and the resistance of the bacteria to antibiotics can be predicted.

6 Claims, 8 Drawing Sheets

Specification includes a Sequence Listing.

(51) Int. Cl.
*C12N 15/88* (2006.01)
*C12Q 1/689* (2018.01)

(58) Field of Classification Search
CPC ........ C12Q 2531/113; C12Q 2563/161; Y02A 50/53; Y02A 50/54; Y02A 50/58; C12N 15/1003; C12N 15/88
See application file for complete search history.

(56) References Cited

FOREIGN PATENT DOCUMENTS

| KR | 10-2009-0081039 A | 7/2009 | | |
|---|---|---|---|---|
| KR | 10-2011-0025603 A | 3/2011 | | |
| KR | 10-1289310 | * | 7/2013 | ............... C12Q 1/68 |
| KR | 10-1289310 B1 | 7/2013 | | |
| WO | 2011127219 A1 | 10/2011 | | |
| WO | WO 2011127219 | * | 10/2011 | ........... C12Q 1/6886 |

OTHER PUBLICATIONS

Y. Kim, et al; Metagenomic analysis of bacteria and bacteria-derived nanovesicles collected from indoor dust; J. Allergy Clin. Immunol., AB18 Abstracts, 2012; 71; 1 page.
International Search Report dated Mar. 31, 2016 for PCT/KR2015/013524.

* cited by examiner

FIG. 1

NOMAL PERSON 1

NOMAL PERSON 2

SEPTIC PATIENT 1

SEPTIC PATIENT 2

SCREENING BIOMARKERS BASED ON METAGENOMIC ANALYSIS

| | CASE | CTL | Avg of CASE | Avg of CTL | ratio |
|---|---|---|---|---|---|
| Propionibacterium acnes (s) | 12 | 5 | 5.27 | 4.48 | 1.18 |
| Novosphingobium (g) | 0 | 1 | 0.00 | 26.62 | 0.00 |
| Skermanella (g) | 1 | 0 | 28.11 | 0.00 | NA |
| Alkalibacterium (g) | 1 | 0 | 5.99 | 0.00 | NA |
| Staphylococcus epidermidis (s) | 1 | 0 | 0.59 | 0.00 | NA |
| Ureaplasma (g) | 1 | 0 | 17.15 | 0.00 | NA |
| Pseudomonas (g) | 11 | 1 | 3.89 | 3.02 | 1.29 |
| Staphylococcus aureus (s) | 6 | 0 | 12.85 | 0.00 | NA |
| Corynebacterium (g) | 1 | 0 | 7.43 | 0.00 | NA |
| Pseudomonas (g) | 1 | 0 | 0.59 | 0.17 | 3.40 |
| Weissella (g) | 1 | 0 | 1.08 | 1.43 | 0.76 |
| Streptococcus (g) | 1 | 0 | 1.94 | 0.00 | NA |
| Caulobacteraceae (f) | 2 | 0 | 14.65 | 1.05 | 13.92 |
| Brevibacterium (g) | 1 | 0 | 5.39 | 0.00 | NA |
| Enterococcus (g) | 4 | 3 | 2.30 | 4.12 | 0.56 |
| Staphylococcus (g) | 1 | 0 | 2.00 | 0.87 | 2.29 |
| Coagulase (-) Staphylococcus (s) | 1 | 0 | 1.80 | 1.40 | 1.28 |
| Brevibacterium (g) | 1 | 0 | 2.48 | 0.00 | NA |
| Kocuria rhizophil (s) | 2 | 0 | 4.73 | 0.00 | NA |
| Bacillus (g) | 2 | 0 | 1.89 | 1.76 | 1.08 |
| Enterobacteriaceae (f) | 2 | 3 | 2.33 | 4.43 | 0.53 |
| Pseudomonas (g) | 3 | 0 | 5.23 | 0.89 | 5.88 |
| Xanthomonadaceae (f) | 3 | 0 | 12.60 | 0.04 | 319.74 |
| Pseudomonas (g) | 15 | 11 | 6.35 | 15.75 | 0.40 |
| Sphingobium (g) | 1 | 0 | 2.55 | 0.13 | 18.96 |
| Enterobacteriaceae (f) | 2 | 2 | 1.94 | 3.77 | 0.51 |
| Enhydrobacter (g) | 1 | 1 | 1.13 | 2.28 | 0.50 |
| Geobacter (g) | 0 | 1 | 0.08 | 6.42 | 0.01 |
| Bacillaceae (f) | 1 | 0 | 0.90 | 1.64 | 0.55 |
| Xanthomonadaceae (f) | 2 | 0 | 1.67 | 0.03 | 56.51 |
| Unassigned | 0 | 1 | 0.00 | 5.33 | 0.00 |
| Erythrobacteraceae (f) | 0 | 1 | 0.28 | 5.21 | 0.05 |

Yellow bar : candidate biomarkers for serious bacterial infection

FIG. 5

| DNA EXTRACTION METHOD | Sample Name | | DNA amount (ng/μl) | A260/A280 | A260/A230 |
|---|---|---|---|---|---|
| THERMAL TREATMENT | PATIENT | UR395 | 2465.5 | 0.78 | 2.46 |
| | | UR415 | 1667.3 | 1.13 | 0.58 |
| | NOMAL PERSON | HC1 | 1920.5 | 0.69 | 11.01 |
| | | HC2 | 1443.9 | 0.79 | 0.53 |
| DNA EXTRACTION KIT | PATIENT | UR395 | 8.1 | 5.77 | 0.54 |
| | | UR415 | 1.4 | 1.89 | 0.59 |
| | NOMAL PERSON | HC1 | -0.1 | 0.6 | -0.05 |
| | | HC2 | 1.6 | 0.9 | 0.67 |
| COMPOUNDS FOR DNA EXTRACTION (PHENOL/CHLOROFORM) | PATIENT | UR395 | 39.7 | 1.51 | 0.56 |
| | | UR415 | 13.4 | 1.16 | 0.43 |
| | NOMAL PERSON | HC1 | 144.4 | 0.71 | 0.36 |
| | | HC2 | 9.2 | 1.06 | 0.35 |

FIG. 7

METHOD FOR IDENTIFYING PATHOGENS OF BACTERIAL INFECTIOUS DISEASES BY USING BACTERIA-DERIVED NANOVESICLES

CROSS-REFERENCE TO RELATED APPLICATIONS

This application is a 371 of PCT/KR2015/013524, filed Dec. 10, 2015, which claims the benefit of priority from Korean Patent Application No. 10-2014-0181580, filed Dec. 16, 2014, the contents of each of which are incorporated herein by reference.

TECHNICAL FIELD

The present invention relates to a method for identifying a causative factor (bacteria) causing a bacterial infectious disease in a clinical sample containing bacteria-derived nano-sized extracellular vesicles, that is, nanovesicles, through the analysis of genes contained in the nanovesicles and simultaneously predicting resistance of the bacteria to antibiotics.

BACKGROUND ART

Serious bacterial infectious diseases are diseases characterized by expressing serious bacterial infections such as pneumonia, infective endocarditis, osteomyelitis, osteoarthritis, meningitis, sepsis, and the like among infectious diseases caused by bacteria, and their incidence rates have increased rapidly with an increase in a group of target patients caused by recent population aging and the spread of multidrug resistant bacteria caused by the indiscriminate use of antibiotics. The multidrug resistant bacteria causing serious bacterial infectious diseases include *Enterococcus* spp., *Staphylococcus aureus, Klebsiella pneumonia*, Acinetobacter baumannii, *Pseudomonas aeruginosa, Enterobacter* spp. as known in the art.

It was reported that serious infections caused by multidrug resistant bacteria generally appear in the form of nosocomial infection, and the mortality rates caused by the serious infections are high, that is, the mortality rates are 5.4% and 29% in the case of pneumonia and sepsis, respectively. Also, a recent survey shows that patients should stay in the hospital for a long time when the patients catch serious bacterial infection, the return on investment spent for treatment is low, and the yearly cost of illness caused by the infection with multidrug resistant bacteria account for at least 1 trillion won in Korea. Moreover, the recent emergence of the multidrug-resistant bacteria in the local communities as well as the nosocomial infections caused by the multidrug resistant bacteria have been reported, and thus is expected to become a big issue on the national health service in the future.

In this regard, methods used to diagnose serious bacterial infectious diseases include biochemical methods, such as a method of identifying bacteria by performing in vitro bacterial cultures on clinical samples such as blood. However, the aforementioned methods based on the analysis results of bacterial genomics (metagenomics) has drawbacks in that it is possible to identify only 1% of the entire bacteria, and a period of at least 5 days is required to perform a bacterial culture. So far, antibiotics have been used based on the clinical experiences without having no information on bacteria.

Meanwhile, it was reported that prokaryotic cells such as bacterial cells and eukaryotic cells such as host cells (for example, human cells) secrete vesicles into the extracellular space, and the secreted vesicles perform various functions. Extracellular vesicles secreted by the bacteria contain endotoxins (lipopolysaccharides; LPS) and bacteria-derived proteins and genes and have a size of 20 to 100 nm, and thus are generally referred to as nanovesicles. It was reported that extracellular vesicles are found in a variety of human or animal secretions, excretion or tissue washes, and it was known that the extracellular vesicles present in tissues reflect the state of tissues secreting the vesicles. Also, it was reported that the extracellular vesicles can be used to diagnose diseases.

However, there is no research conducted on methods for identifying bacteria causing a serious bacterial infection through analysis of genes in bacteria-derived nanovesicles present in the human body and predicting resistance of such bacteria to antibiotics.

DISCLOSURE

Technical Problem

Therefore, the present inventors have found that genes derived from bacteria are present in bacteria-derived nanovesicles derived from a sample separated from a mammalian body, and developed a method capable of predicting a causative factor (bacteria) causing a serious bacterial infection through sequence analysis of genes extracted from the nanovesicles. Therefore, the present invention has been completed based on these facts.

Accordingly, it is an object of the present invention to provide a method for identifying a causative factor (bacteria) causing a serious bacterial infectious disease by extracting genes present in bacteria-derived nanovesicles in a mammalian clinical sample containing the nanovesicles and analyzing sequences of the genes and simultaneously a method for predicting resistance of the bacteria to antibiotics.

However, technical problems to be solved by the present invention are not limited to the technical problems described above, and other technical problems not disclosed herein will be clearly understood from the following description by those skilled in the art.

Technical Solution

According to an aspect of the present invention, there is provided a method for identifying bacteria causing a serious bacterial infectious disease, which includes (A) extracting genes in bacteria-derived nanovesicles from a patient sample containing the nanovesicles;

(B) performing a polymerase chain reaction (PCR) on the extracted genes using a pair of primers set forth in SEQ ID NOS: 1 and 2, and (C) judging that the bacteria causing the serious bacterial infectious disease is present when the yield of the PCR product is increased, compared to a normal person.

According to another aspect of the present invention, there is provided a method for predicting resistance of bacteria causing a serious bacterial infectious disease to antibiotics, which includes (A) extracting genes in bacteria-derived nanovesicles from a patient sample containing the nanovesicles;

(B) performing PCR on the extracted genes using a pair of primers set forth in SEQ ID NOS: 1 and 2; and (C) judging that the bacteria causing the serious bacterial infectious disease has low reactivity to the antibiotics when the yield of the PCR product is increased, compared to a normal person.

According to one exemplary embodiment of the present invention, the patient sample may be selected from the group consisting of urine, blood, an oral fluid, a gastric fluid, feces, a nasal fluid, phlegm, a skin wash, a pleural fluid, a peritoneal fluid, a synovial fluid, a cerebrospinal fluid, an amniotic fluid, and a vaginal wash.

According to another exemplary embodiment of the present invention, the genes in the nanovesicles may include 16S rDNA or 16S rRNA.

According to still another exemplary embodiment of the present invention, the nanovesicles preferably have a mean diameter of 10 to 300 nm, more preferably a mean diameter of 20 to 100 nm.

According to yet another exemplary embodiment of the present invention, the serious bacterial infectious disease may be selected from the group consisting of sepsis, sinusitis, pneumonia, tuberculosis, infective endocarditis, osteoarthritis, osteomyelitis, urinary tract infection, encephalitis, meningitis, and nephritis.

According to yet another exemplary embodiment of the present invention, the bacteria may include multidrug resistant bacteria selected from the group consisting of *Skermanella* sp., *Alkalibacterium* sp., *Ureaplasma* sp., *Corynebacterium* sp., *Streptococcus* sp., *Caulobacteraceae* sp., *Brevibacterium* sp., *Staphylococcus* sp., *Kocuria*, *Pseudomonas* sp., *Xanthomonadaceae* sp., and *Sphingobium* sp.

According to yet another exemplary embodiment of the present invention, the extracting of the genes in step (A) may include (a) centrifuging the patient sample to obtain a supernatant, followed by removal of bacteria and foreign substances through a filter, (b) concentrating the product obtained after the filtering by means of centrifugation, (c) centrifuging the concentrated product at an ultrahigh speed to obtain a nanovesicle pellet, (d) thermally treating the nanovesicle pellet, and (e) centrifuging the thermally treated product to obtain a supernatant.

According to yet another exemplary embodiment of the present invention, the thermal treatment in step (d) may be performed at 90 to 110° C. for 5 to 30 minutes.

Advantageous Effects

According to the method of the present invention, sequences of genes in bacteria-derived nanovesicles in a clinical sample containing the nanovesicles can be analyzed to provide information on bacteria causing bacterial infections and predict a causative factor causing the bacterial infections.

Also, according to the method of the present invention, the information on the bacteria causing bacterial infections can be provided to predict the resistance of the bacteria causing bacterial infections to antibiotics.

BEST MODE

The present invention relates to a method for identifying bacteria causing serious bacterial infections by analyzing sequences of genes in bacteria-derived nanovesicles in a clinical sample such as urine containing the nanovesicles, and thus a method for predicting resistance of the bacteria to antibiotics.

The present inventors have found that nanovesicles secreted from bacteria are absorbed into the human body so that the nanovesicles are circulated in blood to be distributed in various types of mammalian tissues, and then excreted with urine and feces. Accordingly, the present inventors have confirmed that genes (nanovesicles are isolated) are extracted from urine samples of 11 normal persons (controls) and 25 patients with serious bacterial infection, and a sequence of 16S rDNA or 16S rRNA specifically present in bacteria may be analyzed to predict bacteria causing serious bacterial infections.

In this way, the present inventors have confirmed that, when metagenomic analysis is performed on DNA extracted from the nanovesicles, the amount of nanovesicles derived from 12 bacterial genera is significantly increased in urine of patients with serious bacterial infection, compared to that of normal persons.

Also, the present inventors have confirmed that, when the clinical samples are thermally treated, the extracted genes are obtained with an increased purity.

In addition, it is confirmed that, when the genes are extracted from the samples by thermal treatment, followed by metagenomics analysis, the distributions of the bacteria-derived nanovesicle are similar at phylum and genus levels regardless of isolation of the nanovesicles. That is, it can be seen that the same results can be obtained even when the genes in the bacteria-derived nanovesicles are directly extracted from a clinical sample without isolating the nanovesicles, followed by analysis of sequences of the genes.

Further, it is confirmed that, when a genome is extracted from nanovesicles derived from urine samples of normal persons and patients with infective endocarditis and nephritis (APN) using a thermal treatment method and then amplified using 16S rDNA primers so that the amplified products are subjected to metagenomic analysis at a genus level, the amount of the nanovesicles derived from the genus *Staphylococcus* is remarkably increased by approximately 60% or more in urine of the infective endocarditis patients, compared to that of the normal persons, and the amount of the nanovesicles derived from the genus *Caulobacteraceae* is remarkably increased by approximately 40% or more in urine of the nephritis patient.

In this specification, the term "bacterial infection" or "bacterial infectious disease" generally refers to all types of diseases caused by bacteria or bacteria-derived toxins. In general, the bacteria or bacteria-derived toxins breach defense systems of a host to cause infectious diseases. In this case, representative examples of the infectious diseases include pneumonia and pulmonary tuberculosis occurring in the lungs; osteomyelitis and osteoarthritis occurring in bone joints; infective endocarditis occurring in the heart; encephalitis and meningitis occurring in the brain; nephritis occurring in the kidneys; systemically occurring sepsis, etc.

In this specification, the term "serious bacterial infection" or "serious bacterial infectious disease" refers to the expression of serious bacterial infections including cases in which diseases such as pneumonia, sepsis, infective endocarditis, nephritis, osteoarthritis, and the like have a high mortality rate or are difficult to heal due to bacterial infections.

In this specification, the term "predicting a causative factor or bacteria" refers to the expression of serious bacterial infections including cases in which information on bacteria causing infectious diseases caused by the bacteria or bacteria-derived toxins may be provided to use proper antibiotics or predict the course of a disease after the use of antibiotics.

In this specification, the term "predicting resistance to antibiotics" refers to the expression of serious bacterial infections including cases in which information on the resistance of bacteria, which cause infectious diseases caused by the bacteria or bacteria-derived toxins, to antibiotics may be provided to use proper antibiotics or predict the course of a disease after the use of antibiotics.

In this specification, the term "bacteria-derived nanovesicles" refers to nano-sized vesicles secreted by bacteria contained in a clinical sample. In this case, after nanovesicles are isolated from a clinical sample, genes may be extracted from the nanovesicles, or genes contained in nanovesicles may be extracted using a method such as thermal treatment, compound treatment, and the like without isolating the nanovesicles from a clinical sample containing the nanovesicles.

In this specification, the "clinical sample" containing the nanovesicles is a sample obtained from a patient, but the present invention is not limited thereto. However, samples such as blood, urine, phlegm, feces, a nasal fluid, an oral fluid, a synovial fluid, a pleural effusion fluid, a cerebrospinal fluid, and the like may be used according to a purpose.

A method of isolating nanovesicles from the clinical sample such as urine or blood is not particularly limited, and may, for example, include methods such as centrifugation, ultracentrifugation, filtration through filters, gel filtration chromatography, free-flow electrophoresis, capillary electrophoresis, and the like, and combinations thereof. Also, the method may further include a process such as washing to remove impurities, centrifugation, concentration of the resulting nanovesicles, etc.

A method of extracting genes in nanovesicles from the clinical sample may include isolating nanovesicles from a clinical sample and then extracting genes in the nanovesicles using a physical or chemical method, or directly extracting genes in the nanovesicles using a physical or chemical method such as thermal treatment without undergoing a process of isolating nanovesicles from the clinical sample containing the nanovesicles.

The nanovesicles isolated by the method may have a mean diameter of 10 to 300 nm, preferably a mean diameter of 20 to 100 nm.

In this specification, the term "gene" is a concept encompassing bacteria-derived DNA and RNA, and the term "gene sequence analysis" encompasses amplification of a gene using primers complementary to a sequence of the gene.

In this specification, the term "metagenome" is referred to as a 'microbiome,' and refers to a total of genomes including all types of viruses, bacteria, fungi, and the like present in isolated areas such as soil, intestines of an animal, etc. In general, the metagenome is used as a concept of the genome described to identify a lot of microorganisms at once using a DNA sequencer to analyze microorganisms which have not been cultured. In particular, the metagenome does not mean one genome, but refers to a type of mixed genome encompassing all types of genomes in one environmental unit. This is a term derived from an aspect in which one species and various species functionally interact with each other to form a complete species when the one species is omically defined during development of biology. This is a technique of technically analyzing all DNAs and RNAs using a rapid DNA sequencing method regardless of any species so as to identify all types of the species in one environment and elucidate their interactions and metabolisms.

MODE FOR INVENTION

Hereinafter, examples of the present invention will be described in order to aid in understanding the present invention. However, it should be understood that the description set forth herein is merely intended to provide a better understanding of the present invention and is not intended to limit the scope of the present invention.

EXAMPLES

Example 1

Isolation of Nanovesicles from Urine Sample

A urine sample in a 50 ml tube was centrifuged (3,500×g, 10 min, and 4° C.) to precipitate floating materials and obtain a supernatant. Thereafter, bacteria and foreign substances were removed through a 0.22 µm filter. Then, the supernatant was transferred to centripreigugal tubes (centripreigugal filters having a size of 50 kD), centrifuged at 1,500×g and 4° C. for 15 minutes to discard materials having a size of 50 kD or less, and then concentrated to 10 ml. Bacteria and foreign substances were again removed through a 0.22 µm filter, and the concentrated solution was centrifuged at 150,000×g and 4° C. for 3 hours at an ultrahigh speed using a Type 90ti rotor to discard the supernatant. Lumpy pellets were then dissolved in saline solution (PBS). Subsequently, a protein quantification method (a Bradford assay) was performed to measure an amount of nanovesicles. The results are listed in the following Table 1.

TABLE 1

Amount of nanovesicles in urine isolated using ultracentrifugation method

| Samples | Quantitative values of nanovesicles (μg/ml) |
|---|---|
| Normal person 1 | 6 |
| Normal person 2 | 114 |
| Normal person 3 | 8 |
| Normal person 4 | 10 |
| Normal person 5 | 2 |
| Septic patient 1 | 2 |
| Septic patient 2 | 35 |
| Septic patient 3 | 2 |
| Septic patient 4 | 4 |
| Septic patient 5 | 7 |

Example 2

Analysis of Structure and Size of Nanovesicles in Urine Sample

To determine a structure of the nanovesicles isolated in Example 1, the nanovesicles were observed using a transmission electron microscope (JEM 1011 electromicroscopy Jeol, Japan), as follows.

Figure 1:
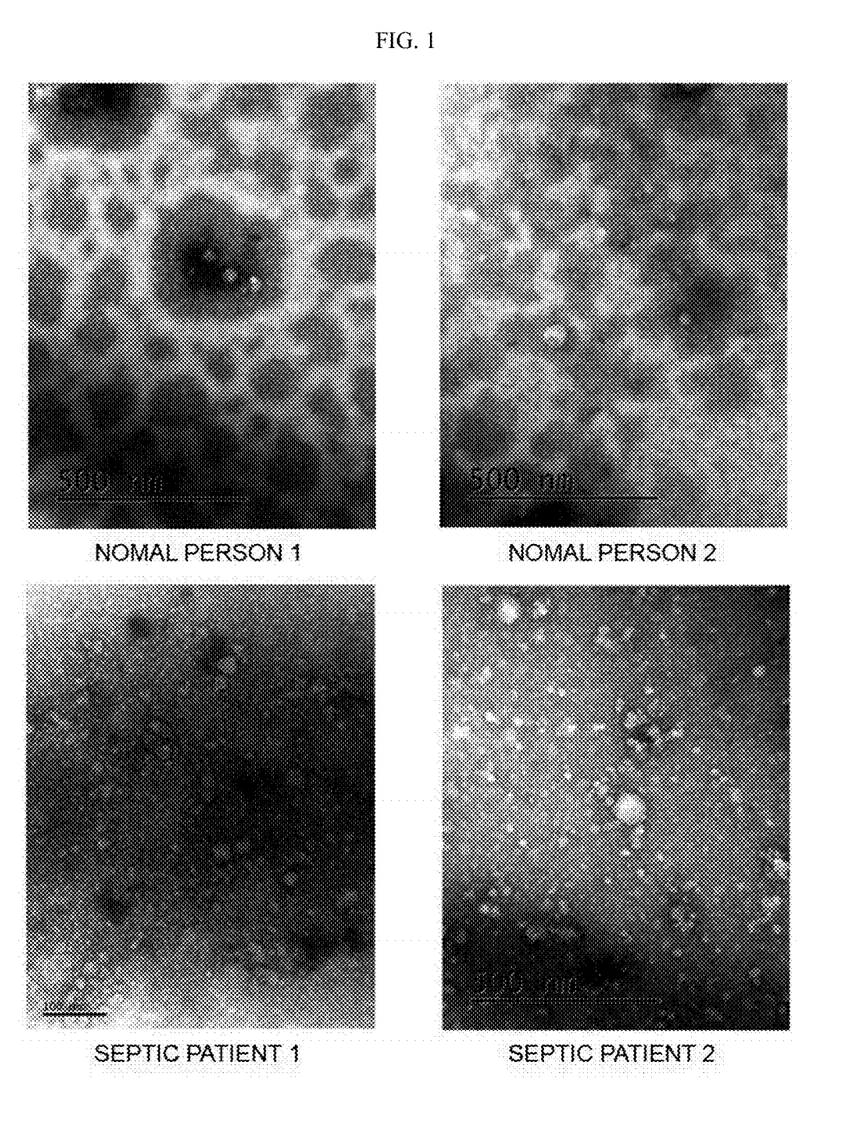
FIG. 1 is an electron microscope image for determining the shapes of nanovesicles in urine samples of normal persons and patients with serious bacterial infection.

First, 20 μl of the nanovesicles was prepared at a concentration of 50 μg/ml, and 7 μl of the nanovesicles was dropped on a surface of a grid for electron microscopic analysis, and adsorbed into the grid for 10 seconds, and a solvent remaining on the grid surface was removed with a piece of tissue. Thereafter, 7 μl of 2% uranyl acetate for negative staining was dropped, and adsorbed into the grid for 10 seconds, and a solvent was also removed with a piece of tissue. Then, the grid was dried at room temperature for 8 hours, and imaged under an electron microscope. The results are shown in FIG. 1.

Figure 2:
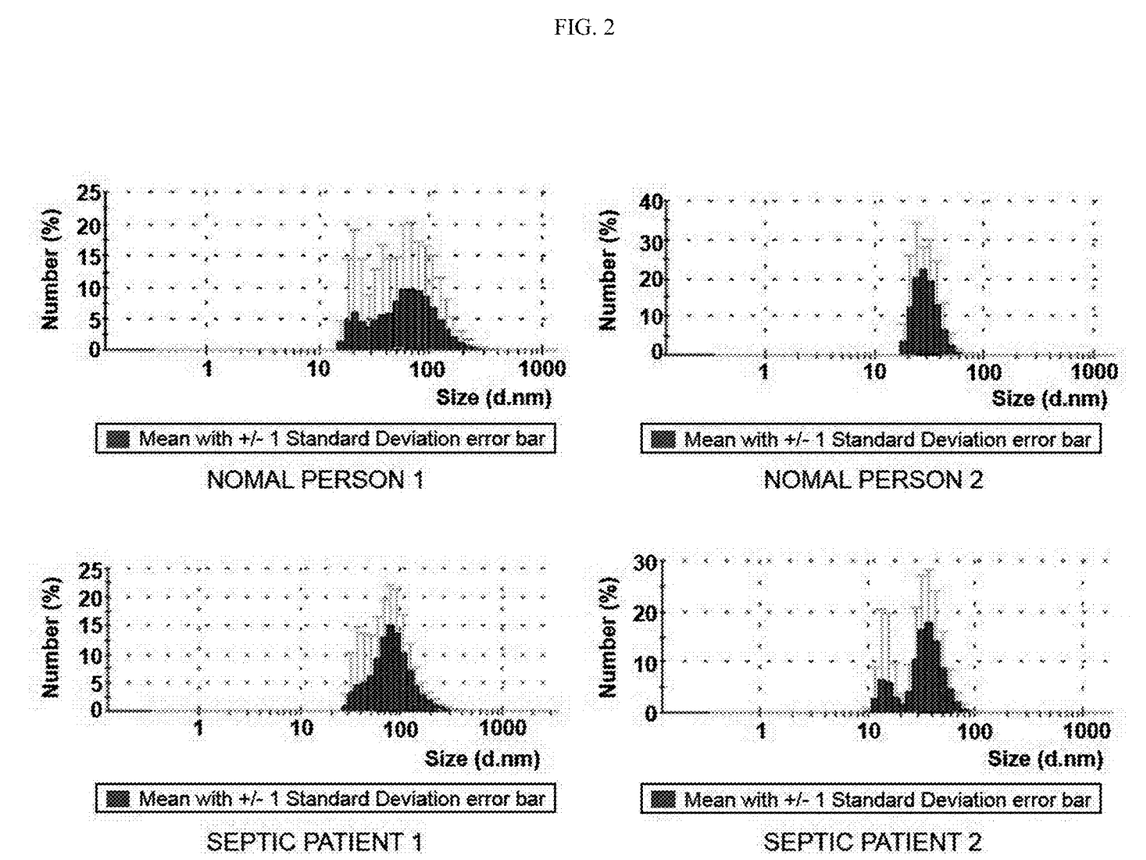
FIG. 2 shows results of measurement using a dynamic light scattering method to determine the sizes of the nanovesicles in urine samples of normal persons and patients with serious bacterial infection.

Also, the size of the nanovesicles isolated by the method of Example 1 was measured using a dynamic light scattering method (Zetasizer nano ZS Malverk, UK). 1 ml of the nanovesicles was prepared at a concentration of 5 μg/ml, transferred to a cuvette (ZEN0112) to be positioned in place, and then imaged three times in 30 cycles. As a result, it was revealed that the nanovesicles had a diameter of approximately 10 to 100 nm, as shown in FIG. 2.

Example 3

Extraction of DNA from Nanovesicles (Thermal Treatment Method)

Genes were not extracted when DNA was extracted from a urine sample using a conventional DNA extraction kit. To solve this problem, a thermal treatment method was performed, as follows.

First, 100 μl of the nanovesicles isolated by the method of Example 1 was thermally treated on a heat block at 100° C. for 15 minutes so that DNA in the vesicles exuded out of a lipid membrane, and then cooled on ice for 5 minutes. To remove the remaining floating materials, the exudate was centrifuged at 10,000×g and 4° C. for 30 minutes to collect only a supernatant. Then, DNA was quantified using a Nano spectrophotometer (Nanodrop). As a result, 1,000 to 1,500 ng of DNA was extracted per 1 μl of urine.

Figure 3:
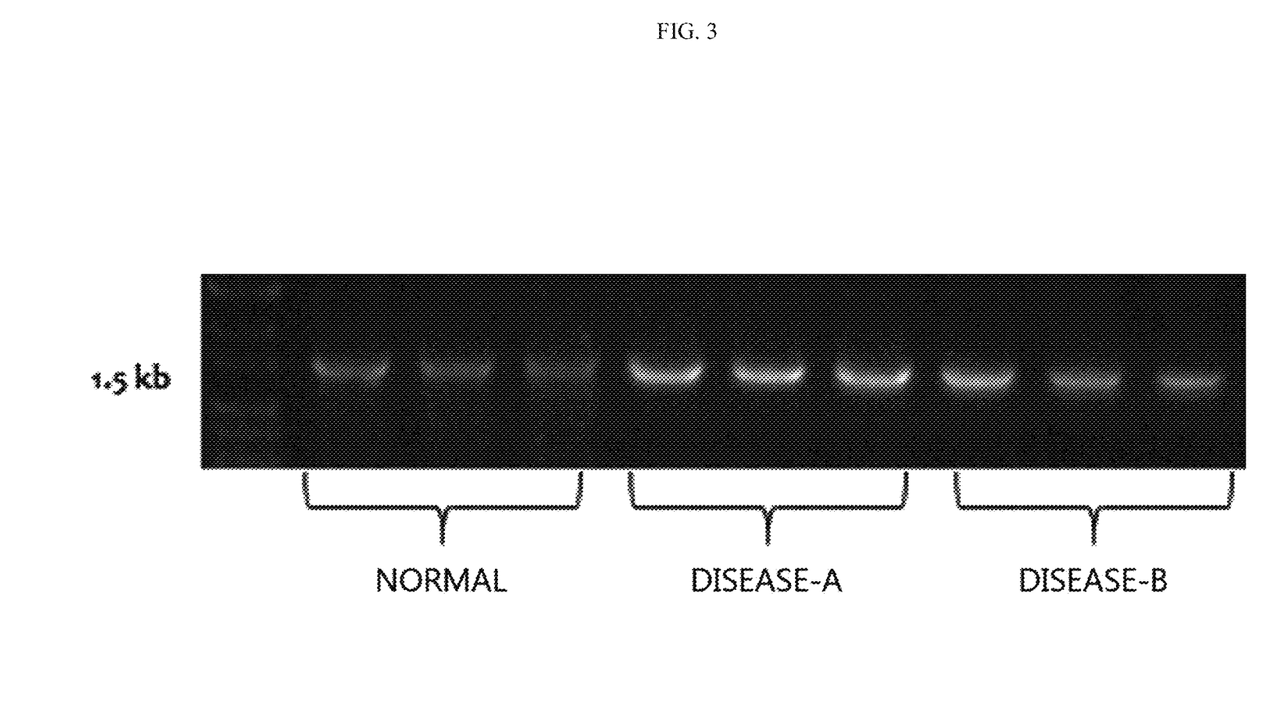
FIG. 3 shows PCR results of determining whether there are bacteria-derived genes in nanovesicles isolated from the urine samples of normal persons and patients with serious bacterial infection.

Next, to determine whether a bacteria-derived gene is present in the extracted DNA, PCR was performed using the following 16S rDNA primers. As a result, it was confirmed that the bacteria-derived gene was present in septic patients 1 and 2, as shown in FIG. 3.

```
Forward primer:
                                        (SEQ ID NO: 1)
5'-AGA GTT TGA TCM TGG CTC AG-3'
(Base M refers to A or C)

Reverse primer:
                                        (SEQ ID NO: 2)
5'-GGT TAC CTT GTT ACG ACT T-3'
```

Example 4

Metagenomic Analysis Using DNA Extracted from Nanovesicles

Nanovesicles were isolated from urine samples of 11 normal persons and 25 patients with serious bacterial infectious disease using the method of Example 1. Thereafter, DNA was extracted from the nanovesicles using the thermal treatment method of Example 3, PCR-amplified using a pair of 16S rDNA primers (SEQ ID NOS: 1 and 2), and then sequenced (Roche GS FLX sequencer).

The results were output in the form a Standard Flowgram Format (SFF) file. Thereafter, the SFF file was converted into a sequence file (.fasta) and a nucleotide quality score file using GS FLX software (v2.9). Then, the lead's credit rating was confirmed, a portion of a base window (20 bps) having a mean base call accuracy of less than 99% (Phred score<20) was removed, and only base windows in which reads had a length of 300 bp or more were used (Sickle version 1.33).

For operational taxonomy unit (OTU) analysis, clustering was performed according to the sequence similarity using UCLUST and USEARCH, the genus, family, order, class and phylum were clustered based on the sequence similarities of 94%, 90%, 85%, 80%, and 75%, respectively. Then, after levels of the phylum, class, order, family and genus of respective OTUs were classified, bacteria having a sequence similarity of 97% or more were analyzed using BLASTN and GreenGenes 16S rDNA sequence database (108,453 sequences) (QIIME).

In this case, when it was assumed that the average distribution ratios of the respective groups differed 2-fold or more and the p value was 0.05 in the statistical analysis, bacteria which were present at significantly different ratios in the control and experimental groups were selected using a t-test.

Figure 4A:
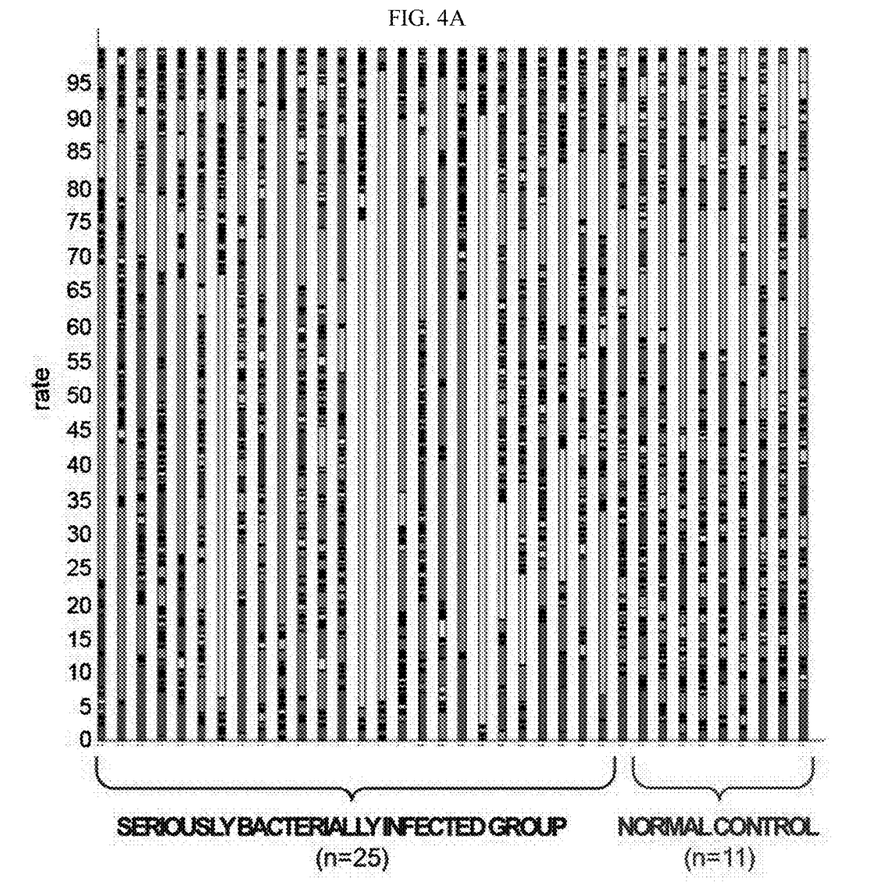
FIG. 4A shows results of metagenomic analysis of the nanovesicles isolated from the urine samples of the normal persons and patients with serious bacterial infection.
Figure 4B:
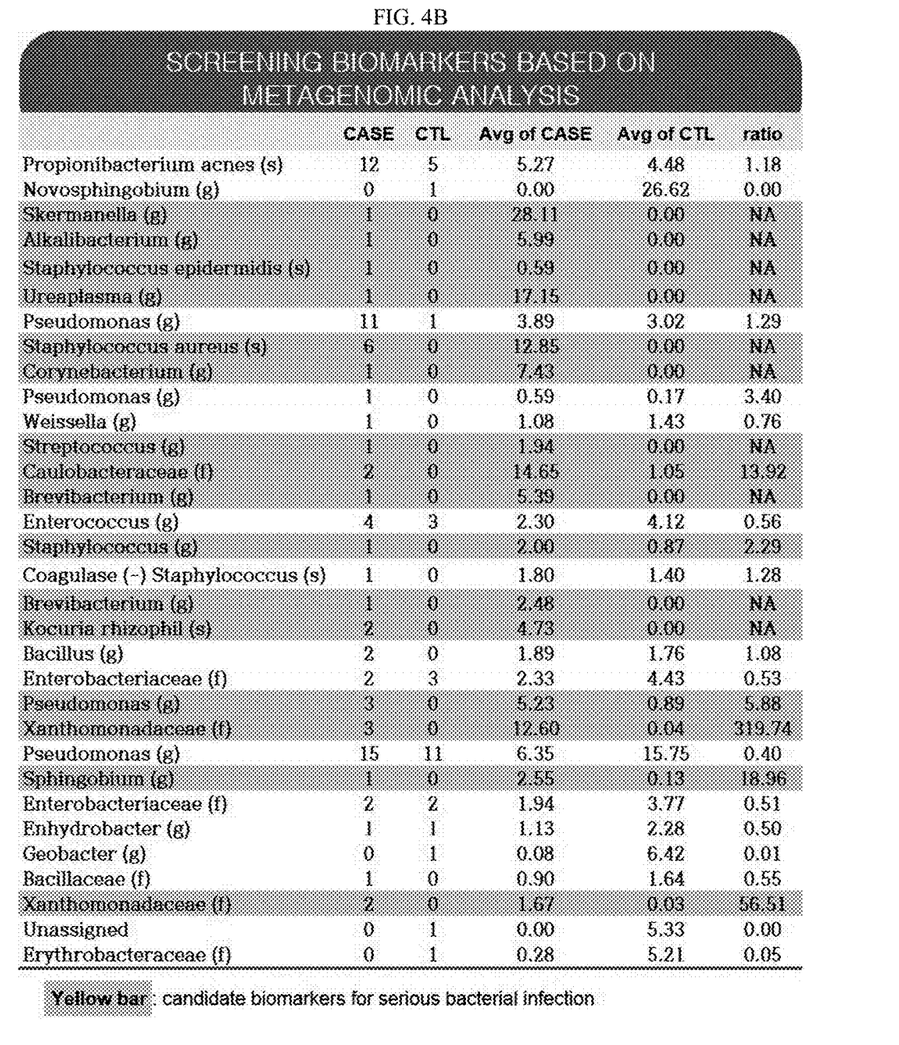
FIG. 4B shows results showing a list of bacteria (highlighted in yellow) in which the amount of nanovesicles is increased in the patients with serious bacterial infection, compared to the normal persons.

Also, the similarities between the samples were analyzed using hierarchical clustering, principal component analysis (PCA), etc. As a result, it was revealed that the amount of the nanovesicles derived from 12 bacterial genera was significantly increased in urine of the patients with serious bacterial infection, compared to that of the normal persons, as shown in FIG. 4. Specifically, FIG. 4A shows results of metagenomic analysis of the nanovesicles isolated from the urine samples of normal persons and patients with serious bacterial infection, and FIG. 4B shows results showing a list of bacteria (highlighted in yellow) in which the amount of nanovesicles is increased in the patients with serious bacterial infection, compared to the normal persons. In this case, it can be seen that the amount of nanovesicles was increased in the 12 species such as *Skermanella* sp., *Alkalibacterium* sp., *Ureaplasma* sp., *Corynebacterium* sp., *Streptococcus* sp., *Caulobacteraceae* sp., *Brevibacterium* sp., *Staphylococcus* sp., *Kocuria, Pseudomonas* sp., *Xanthomonadaceae* sp., and *Sphingobium* sp.

Example 5

Difference in Amount of Extracted DNA According to Thermal Treatment of Nanovesicles, Kit, and Compound Treatment After DNA was extracted from the nanovesicles in urine of the normal persons and patients with serious bacterial infectious disease using the thermal treatment method of Example 3, it was determined whether an amount of extracted DNA was different, compared to when a DNA extraction kit (Bioneer Inc.) and compounds (phenol/chloroform extraction) for DNA extraction were used.

Figure 5:
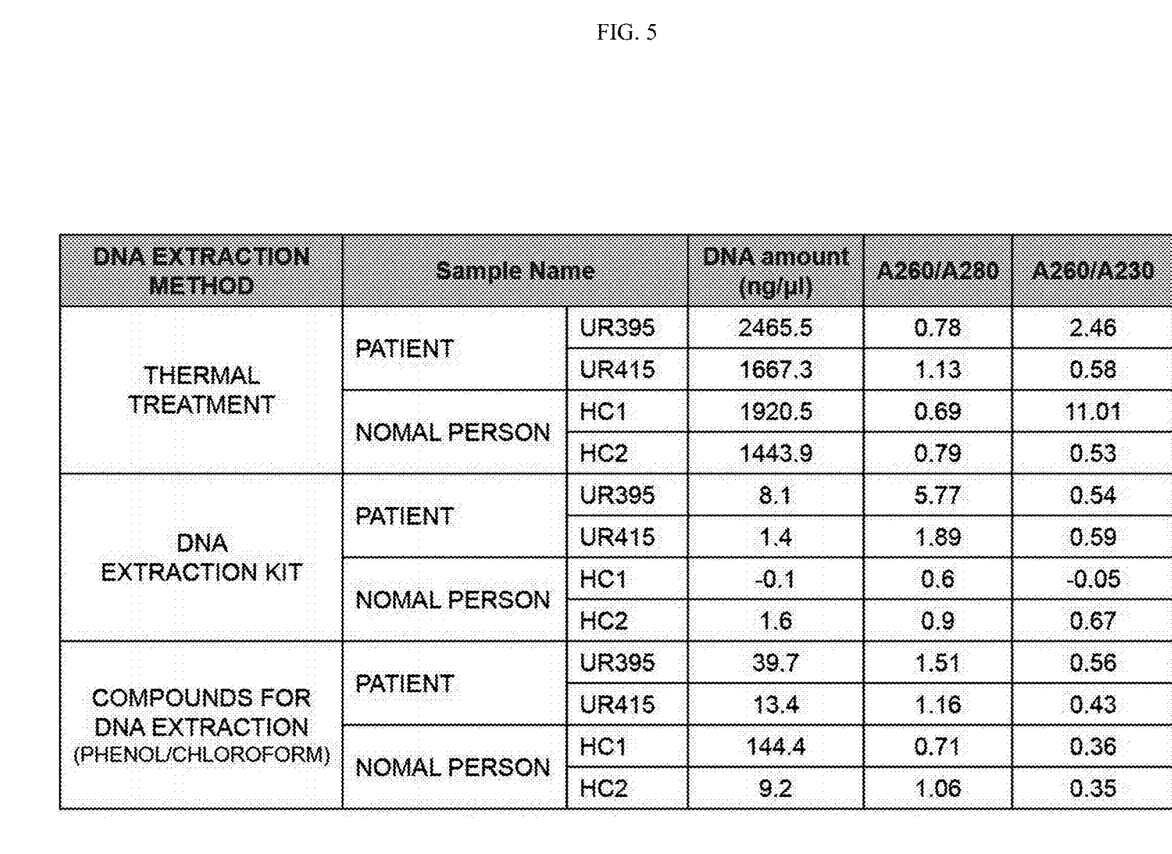
FIG. 5 shows results of showing differences in amounts of extracted DNA in urine samples of normal persons and patients with serious bacterial infection, depending on a thermal treatment method, a DNA extraction kit, and compound (phenol/chloroform) treatment for DNA extraction.

As a result, it can be seen that DNA was hardly extracted when the DNA extraction kit was used and an amount of extracted DNA was increased when the DNA was extracted with a phenol/chloroform compound, compared to when the kit was used, as shown in FIG. 5. However, it was revealed that an amount of extracted DNA was remarkably high when extracted by the thermal treatment method of Example 3, compared to the other methods.

Example 6

Analysis of Difference in Distribution of Bacteria-Derived Nanovesicles According to Isolation of Nanovesicles To compare a difference in distribution of the bacteria-derived nanovesicles according to the isolation of the nanovesicles, DNA was extracted after the nanovesicles isolated from the urine samples were thermally treated and after the urine samples themselves were thermally treated without independent isolation of the nanovesicles, and subjected to metagenomic analysis using the method of Example 4.

Figure 6:
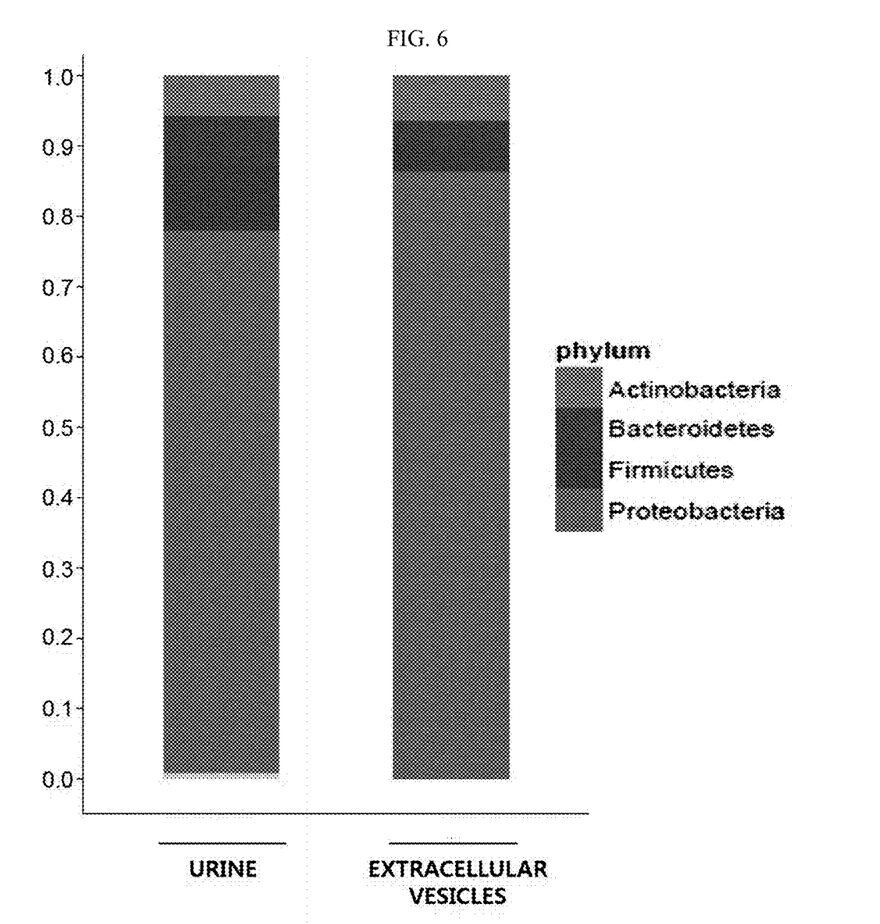
FIG. 6 shows results of performing metagenomic analysis on nanovesicles at a phylum level after the nanovesicles are isolated from a urine sample and then thermally treated, or a urine sample is directly thermally treated.
Figure 7:
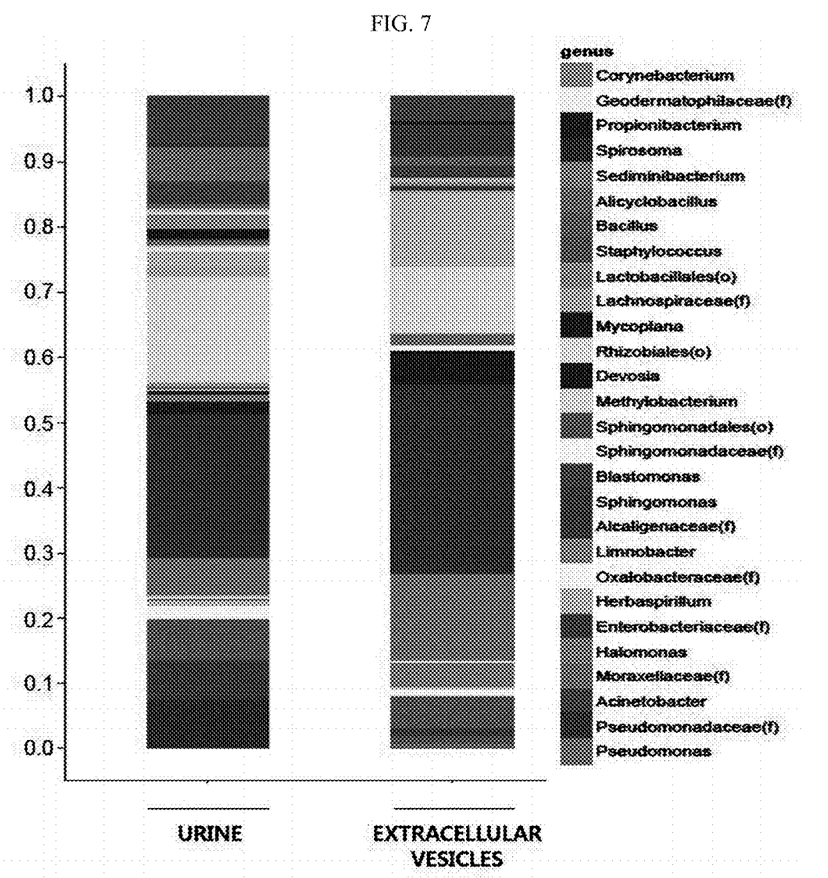
FIG. 7 shows results of performing metagenomic analysis on nanovesicles at a genus level after the nanovesicles are isolated from a urine sample and then thermally treated, or a urine sample is directly thermally treated.

As a result, it can be seen that the distributions of the bacteria-derived nanovesicles was similar at phylum and genus levels in both the urine-thermally treated groups and the extracellular vesicle-thermally treated groups regardless of isolation of the nanovesicles, as shown in FIGS. 6 and 7.

Example 7

Metagenomic Analysis Performed by Extracting Genes from Urine of Infective Endocarditis Patient Using Thermal Treatment Method For the 10 urine samples of each of the normal persons and infective endocarditis patients, the genome extracted by the thermal treatment method of Example 3 was PCR-amplified using a pair of 16S rDNA primers (SEQ ID NOS: 1 and 2), and then subjected to metagenomic analysis using the method of Example 4. As a result, it was revealed that the amount of the nanovesicles derived from the genus *Staphylococcus* was remarkably increased by 61% in the urine of the infective endocarditis patients, compared to that of the normal persons.

Example 8

Metagenomic Analysis Performed by Extracting Genes from Urine of Nephritis Patient Using Thermal Treatment Method For the 10 urine samples of each of the normal persons and nephritis (APN) patients, the genome extracted by the thermal treatment method of Example 3 was PCR-amplified using a pair of 16S rDNA primers (SEQ ID NOS: 1 and 2), and then subjected to metagenomic analysis using the method of Example 4. As a result, it was revealed that the amount of the nanovesicles derived from the genus *Caulobacteraceae* was remarkably increased by 46% in the urine of the nephritis patients, compared to that of the normal persons.

While the present invention has been shown and described with reference to certain exemplary embodiments thereof, it will be understood by those skilled in the art that various changes in form and details may be made therein without departing from the spirit and scope of the invention as defined by the appended claims.

---

The invention claimed is:

1. A method for identifying bacteria causing a bacterial infectious disease, comprising: (A) extracting genes in bacteria-derived nanovesicles from a patient sample containing the nanovesicles by (a) centrifuging the patient sample to obtain a supernatant, followed by removal of bacteria and foreign substances through a filter; (b) concentrating the product obtained after the filtering by means of centrifugation; (c) centrifuging the concentrated product at an ultra-high speed to obtain a nanovesicle pellet; (d) thermally treating the nanovesicle pellet; and (e) centrifuging the thermally treated product to obtain a supernatant containing the extracted genes; (B) performing a polymerase chain reaction (PCR) on the extracted genes using a pair of primers set forth in SEQ ID NOS: 1 and 2 to yield a PCR product; (C) measuring the yield of the PCR product; and (D) comparing said yield of the PCR product to the amount of nanovesicles derived from multidrug resistant bacteria present in a sample of a normal person to diagnose the bacterial infection disease selected from the group consisting of sepsis, sinusitis, pneumonia, tuberculosis, infective endocarditis, osteoarthritis, osteomyelitis, urinary tract infection, encephalitis, meningitis, and nephritis wherein the method does not include a pre-amplification of said nanovesicle pellet.

2. The method of claim 1, wherein the patient sample is selected from the group consisting of urine, blood, an oral fluid, a gastric fluid, feces, a nasal fluid, phlegm, a skin wash, a pleural fluid, a peritoneal fluid, a synovial fluid, a cerebrospinal fluid, an amniotic fluid, and a vaginal wash.

3. The method of claim 1, wherein the genes in the nanovesicles comprise 16S rDNA or 16S rRNA.

4. The method of claim 1, wherein the nanovesicles have a mean diameter of 10 to 300 nm.

5. The method of claim 1, wherein the multidrug resistant bacteria is selected from the group consisting of *Skermanella* sp., *Alkalibacterium* sp., *Ureaplasma* sp., *Corynebacterium* sp., *Streptococcus* sp., *Caulobacteraceae* sp., *Brevibacterium* sp., *Staphylococcus* sp., *Kocuria, Pseudomonas* sp., *Xanthomonadaceae* sp., and *Sphingobium* sp.

6. The method of claim 1, wherein the thermal treatment in step (d) is performed at 90 to 110° C. for 5 to 30 minutes.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Forward Primer for 16s rDNA

<400> SEQUENCE: 1
agagtttgat cmtggctcag                                           20

<210> SEQ ID NO 2
<211> LENGTH: 19
<212> TYPE: DNA
<213> ORGANISM: Artificial Sequence
<220> FEATURE:
<223> OTHER INFORMATION: Reverse Primer for 16s rDNA

<400> SEQUENCE: 2
ggttaccttg ttacgactt                                            19